US011128076B2

(12) United States Patent
Villarreal et al.

(10) Patent No.: US 11,128,076 B2
(45) Date of Patent: Sep. 21, 2021

(54) CONNECTOR RECEPTACLE

(71) Applicant: Cadwell Laboratories, Inc., Kennewick, WA (US)

(72) Inventors: Richard A. Villarreal, West Richland, WA (US); David Lee Jepsen, Kennewick, WA (US)

(73) Assignee: Cadwell Laboratories, Inc., Kennewick, WA (US)

( * ) Notice: Subject to any disclaimer, the term of this patent is extended or adjusted under 35 U.S.C. 154(b) by 0 days.

(21) Appl. No.: 16/747,748

(22) Filed: Jan. 21, 2020

(65) Prior Publication Data
US 2020/0235512 A1    Jul. 23, 2020

Related U.S. Application Data

(60) Provisional application No. 62/794,884, filed on Jan. 21, 2019.

(51) Int. Cl.
| | | |
|---|---|---|
| *H01R 13/11* | (2006.01) | |
| *H01R 13/52* | (2006.01) | |
| *H01R 13/24* | (2006.01) | |
| *A61B 5/296* | (2021.01) | |
| *H01R 107/00* | (2006.01) | |

(52) U.S. Cl.
CPC ....... *H01R 13/111* (2013.01); *H01R 13/2485* (2013.01); *H01R 13/5202* (2013.01); *A61B 5/296* (2021.01); *H01R 2107/00* (2013.01)

(58) Field of Classification Search
CPC .. H01R 13/111; H01R 13/2485; H01R 13/52; H01R 13/5202; H01R 39/12; H01R 39/643
See application file for complete search history.

(56) References Cited

U.S. PATENT DOCUMENTS

| 751,475 A | 2/1904 | De Vilbiss |
| 2,320,709 A | 6/1943 | Arnesen |
| 2,807,259 A | 9/1957 | Guerriero |

(Continued)

FOREIGN PATENT DOCUMENTS

| DE | 102014008684 A1 | 1/2016 |
| EP | 298268 | 1/1989 |

(Continued)

OTHER PUBLICATIONS

Aage R. Møller, "Intraoperative Neurophysiologic Monitoring", University of Pittsburgh, School of Medicine Pennsylvania, © 1995 by Harwood Academic Publishers GmbH.

(Continued)

*Primary Examiner* — Oscar C Jimenez
(74) *Attorney, Agent, or Firm* — Novel IP

(57) ABSTRACT

A connector receptacle for connecting with a corresponding connector plug coupled with electrodes being used for performing EMG procedure on a patient is provided. The receptacle includes a first ball bearing pressing against a first end of a housing of the plug and, preferably, a second ball bearing pressing against a first end of the housing of the plug when the plug is connected to the receptacle for exerting a retention force against the plug. The first and the second ball bearings are pressed against the first and the second ends respectively by using a spring force generated, for example, by a retention band.

21 Claims, 11 Drawing Sheets

(56) References Cited

U.S. PATENT DOCUMENTS

| | | | |
|---|---|---|---|
| 3,165,340 A * | 1/1965 | Kuehl | H01R 13/623 285/316 |
| 3,659,250 A * | 4/1972 | Horton | H01R 13/6276 439/348 |
| 3,682,162 A | 8/1972 | Colyer | |
| 3,985,125 A | 10/1976 | Rose | |
| 3,993,859 A * | 11/1976 | McNeel | G01V 1/16 174/565 |
| 4,155,353 A | 5/1979 | Rea | |
| 4,262,306 A | 4/1981 | Renner | |
| 4,263,899 A | 4/1981 | Burgin | |
| 4,545,374 A | 10/1985 | Jacobson | |
| 4,562,832 A | 1/1986 | Wilder | |
| 4,616,635 A | 10/1986 | Caspar | |
| 4,705,049 A | 11/1987 | John | |
| 4,716,901 A | 1/1988 | Jackson | |
| 4,743,959 A | 5/1988 | Frederiksen | |
| 4,765,311 A | 8/1988 | Kulik | |
| 4,817,587 A | 4/1989 | Janese | |
| 4,862,891 A | 9/1989 | Smith | |
| 4,889,502 A | 12/1989 | Althouse | |
| 4,914,508 A | 4/1990 | Music | |
| 5,107,845 A | 4/1992 | Guern | |
| 5,171,279 A | 12/1992 | Mathews | |
| 5,196,015 A | 3/1993 | Neubardt | |
| 5,284,153 A | 2/1994 | Raymond | |
| 5,284,154 A | 2/1994 | Raymond | |
| 5,299,563 A | 4/1994 | Seton | |
| 5,377,667 A | 1/1995 | Patton | |
| 5,438,989 A | 8/1995 | Hochman | |
| 5,462,448 A | 10/1995 | Kida | |
| 5,472,426 A | 12/1995 | Bonati | |
| 5,474,558 A | 12/1995 | Neubardt | |
| 5,540,235 A | 7/1996 | Wilson | |
| 5,544,286 A | 8/1996 | Laney | |
| 5,560,372 A | 10/1996 | Cory | |
| 5,565,779 A | 10/1996 | Arakawa | |
| 5,578,060 A | 11/1996 | Pohl | |
| 5,601,608 A | 2/1997 | Mouchawar | |
| 5,602,585 A | 2/1997 | Dickinson | |
| 5,625,759 A | 4/1997 | Freeman | |
| 5,648,815 A | 7/1997 | Toba | |
| 5,664,029 A | 9/1997 | Callahan | |
| 5,681,265 A | 10/1997 | Maeda | |
| 5,684,887 A | 11/1997 | Lee | |
| 5,728,046 A | 3/1998 | Mayer | |
| 5,741,261 A | 4/1998 | Moskovitz | |
| 5,772,661 A | 6/1998 | Michelson | |
| 5,775,331 A | 7/1998 | Raymond | |
| 5,775,931 A | 7/1998 | Jones | |
| 5,785,648 A | 7/1998 | Min | |
| 5,792,044 A | 8/1998 | Foley | |
| 5,795,291 A | 8/1998 | Koros | |
| 5,830,150 A | 11/1998 | Palmer | |
| 5,847,755 A | 12/1998 | Wixson | |
| 5,860,973 A | 1/1999 | Michelson | |
| 5,868,668 A | 2/1999 | Weiss | |
| 5,885,210 A | 3/1999 | Cox | |
| 5,891,147 A | 4/1999 | Moskovitz | |
| 5,928,139 A | 7/1999 | Koros | |
| 5,928,158 A | 7/1999 | Aristides | |
| 5,930,379 A | 7/1999 | Rehg | |
| 5,931,777 A | 8/1999 | Sava | |
| 5,933,929 A | 8/1999 | Kawakami | |
| 5,944,658 A | 8/1999 | Koros | |
| 5,954,635 A | 9/1999 | Foley | |
| 5,993,385 A | 11/1999 | Johnston | |
| 6,004,312 A | 12/1999 | Finneran | |
| 6,004,341 A | 12/1999 | Zhu | |
| 6,026,180 A | 2/2000 | Wittenstein | |
| 6,042,540 A | 3/2000 | Johnston | |
| 6,062,216 A | 5/2000 | Corn | |
| 6,074,343 A | 6/2000 | Nathanson | |
| 6,088,878 A | 7/2000 | Antonucci | |
| 6,095,987 A | 8/2000 | Shmulewitz | |
| 6,109,948 A | 8/2000 | Kuo | |
| 6,116,941 A | 9/2000 | Kuo | |
| 6,119,306 A | 9/2000 | Antonucci | |
| 6,139,493 A | 10/2000 | Koros | |
| 6,152,871 A | 11/2000 | Foley | |
| 6,181,961 B1 | 1/2001 | Prass | |
| 6,196,969 B1 | 3/2001 | Bester | |
| 6,206,826 B1 | 3/2001 | Mathews | |
| 6,210,202 B1 | 4/2001 | Kuo | |
| 6,224,545 B1 | 5/2001 | Cocchia | |
| 6,236,874 B1 | 5/2001 | Devlin | |
| 6,241,548 B1 | 6/2001 | Kuo | |
| 6,259,945 B1 | 7/2001 | Epstein | |
| 6,264,491 B1 | 7/2001 | Lord | |
| 6,266,558 B1 | 7/2001 | Gozani | |
| 6,273,740 B1 | 8/2001 | Lord | |
| 6,287,322 B1 | 9/2001 | Zhu | |
| 6,302,842 B1 | 10/2001 | Auerbach | |
| 6,306,100 B1 | 10/2001 | Prass | |
| 6,309,349 B1 | 10/2001 | Bertolero | |
| 6,325,764 B1 | 12/2001 | Griffith | |
| 6,334,068 B1 | 12/2001 | Hacker | |
| 6,373,890 B1 | 4/2002 | Freeman | |
| 6,425,859 B1 | 7/2002 | Foley | |
| 6,450,952 B1 | 9/2002 | Rioux | |
| 6,466,817 B1 | 10/2002 | Kaula | |
| 6,473,639 B1 | 10/2002 | Fischell | |
| 6,500,128 B2 | 12/2002 | Marino | |
| 6,535,759 B1 | 3/2003 | Epstein | |
| 6,579,114 B2 | 6/2003 | Lord | |
| 6,609,018 B2 | 8/2003 | Cory | |
| 6,712,795 B1 | 3/2004 | Cohen | |
| 6,799,931 B2 | 10/2004 | Kwilosz | |
| 6,805,668 B1 | 10/2004 | Cadwell | |
| 6,837,716 B1 | 1/2005 | Brazas | |
| 6,847,849 B2 | 1/2005 | Mamo | |
| 6,851,430 B2 | 2/2005 | Tsou | |
| 6,869,301 B2 | 3/2005 | Shimizu | |
| 6,870,109 B1 | 3/2005 | Villarreal | |
| 6,926,728 B2 | 8/2005 | Zucherman | |
| 6,945,933 B2 | 9/2005 | Branch | |
| 7,072,521 B1 | 7/2006 | Cadwell | |
| 7,089,059 B1 | 8/2006 | Pless | |
| 7,104,965 B1 | 9/2006 | Jiang | |
| 7,177,677 B2 | 2/2007 | Kaula | |
| 7,214,197 B2 | 5/2007 | Prass | |
| 7,230,688 B1 | 6/2007 | Villarreal | |
| 7,261,688 B2 | 8/2007 | Smith | |
| 7,374,448 B1 | 5/2008 | Jepsen | |
| 7,470,236 B1 | 12/2008 | Kelleher | |
| 7,522,953 B2 | 4/2009 | Kaula | |
| 7,713,210 B2 | 5/2010 | Byrd | |
| 7,801,601 B2 | 9/2010 | Maschino | |
| 7,914,350 B1 | 3/2011 | Bozich | |
| 7,963,927 B2 | 6/2011 | Kelleher | |
| 7,983,761 B2 | 7/2011 | Giuntoli | |
| 8,147,421 B2 | 4/2012 | Farquhar | |
| 8,160,694 B2 | 4/2012 | Salmon | |
| 8,192,437 B2 | 6/2012 | Simonson | |
| D670,656 S | 11/2012 | Jepsen | |
| 8,323,208 B2 | 12/2012 | Davis | |
| 8,439,703 B2 * | 5/2013 | Natoli | H01R 24/564 439/578 |
| 8,876,813 B2 | 11/2014 | Min | |
| 8,942,797 B2 | 1/2015 | Bartol | |
| 8,958,869 B2 | 2/2015 | Kelleher | |
| 9,084,551 B2 | 7/2015 | Brunnett | |
| 9,138,586 B2 * | 9/2015 | Eiger | A61N 1/3752 |
| 9,155,503 B2 | 10/2015 | Cadwell | |
| 9,295,401 B2 | 3/2016 | Cadwell | |
| 9,352,153 B2 | 5/2016 | Van Dijk | |
| 9,730,634 B2 | 8/2017 | Cadwell | |
| 2002/0007188 A1 | 1/2002 | Arambula | |
| 2002/0009916 A1 | 1/2002 | Lord | |
| 2002/0088098 A1 | 7/2002 | Bouley | |
| 2002/0095080 A1 | 7/2002 | Cory | |
| 2003/0045808 A1 | 3/2003 | Kaula | |
| 2003/0074033 A1 | 4/2003 | Pless | |
| 2004/0030258 A1 | 2/2004 | Williams | |

(56) References Cited

U.S. PATENT DOCUMENTS

| | | |
|---|---|---|
| 2004/0127810 A1 | 7/2004 | Sackellares |
| 2004/0192100 A1 | 9/2004 | Shimizu |
| 2005/0003682 A1 | 1/2005 | Brazas |
| 2005/0075578 A1 | 4/2005 | Gharib |
| 2005/0182454 A1 | 8/2005 | Gharib |
| 2006/0009754 A1 | 1/2006 | Boese |
| 2006/0085048 A1 | 4/2006 | Cory |
| 2006/0085049 A1 | 4/2006 | Cory |
| 2006/0122514 A1 | 6/2006 | Byrd |
| 2006/0135877 A1 | 6/2006 | Giftakis |
| 2006/0258951 A1 | 11/2006 | Bleich |
| 2007/0016097 A1 | 1/2007 | Farquhar |
| 2007/0021682 A1 | 1/2007 | Gharib |
| 2007/0032841 A1 | 2/2007 | Urmey |
| 2007/0049962 A1 | 3/2007 | Marino |
| 2007/0184422 A1 | 8/2007 | Takahashi |
| 2007/0202005 A1 | 8/2007 | Maschke |
| 2008/0027507 A1 | 1/2008 | Bijelic |
| 2008/0058606 A1 | 3/2008 | Miles |
| 2008/0065144 A1 | 3/2008 | Marino |
| 2008/0071191 A1 | 3/2008 | Kelleher |
| 2008/0082136 A1 | 4/2008 | Gaudiani |
| 2008/0097164 A1 | 4/2008 | Miles |
| 2008/0108244 A1 | 5/2008 | Jepsen |
| 2008/0167574 A1 | 7/2008 | Farquhar |
| 2008/0183096 A1 | 7/2008 | Snyder |
| 2008/0194970 A1 | 8/2008 | Steers |
| 2008/0269777 A1 | 10/2008 | Appenrodt |
| 2008/0281313 A1 | 11/2008 | Fagin |
| 2008/0312520 A1 | 12/2008 | Rowlandson |
| 2009/0018399 A1 | 1/2009 | Martinelli |
| 2009/0088660 A1 | 4/2009 | McMorrow |
| 2009/0105604 A1 | 4/2009 | Bertagnoli |
| 2009/0177112 A1 | 7/2009 | Gharib |
| 2009/0196471 A1 | 8/2009 | Goetz |
| 2009/0204016 A1 | 8/2009 | Gharib |
| 2009/0209879 A1 | 8/2009 | Kaula |
| 2009/0259108 A1 | 10/2009 | Miles |
| 2009/0279767 A1 | 11/2009 | Kukuk |
| 2010/0036384 A1 | 2/2010 | Gorek |
| 2010/0106011 A1 | 4/2010 | Byrd |
| 2010/0113898 A1 | 5/2010 | Kim |
| 2010/0152604 A1 | 6/2010 | Kaula |
| 2010/0168603 A1 | 7/2010 | Himes |
| 2010/0191305 A1 | 7/2010 | Imran |
| 2010/0249638 A1 | 9/2010 | Liley |
| 2010/0286554 A1 | 11/2010 | Davis |
| 2010/0317931 A1 | 12/2010 | Sarkela |
| 2010/0317989 A1 | 12/2010 | Gharib |
| 2011/0082383 A1 | 4/2011 | Cory |
| 2011/0184308 A1 | 7/2011 | Kaula |
| 2011/0295579 A1 | 12/2011 | Tang |
| 2011/0313530 A1 | 12/2011 | Gharib |
| 2012/0003862 A1 | 1/2012 | Newman |
| 2012/0071779 A1 | 3/2012 | Sarkela |
| 2012/0109000 A1 | 5/2012 | Kaula |
| 2012/0109004 A1 | 5/2012 | Cadwell |
| 2012/0209082 A1 | 8/2012 | Al-Ali |
| 2012/0220891 A1 | 8/2012 | Kaula |
| 2012/0238893 A1 | 9/2012 | Farquhar |
| 2012/0265040 A1 | 10/2012 | Ito |
| 2012/0296230 A1 | 11/2012 | Davis |
| 2013/0012880 A1 | 1/2013 | Blomquist |
| 2013/0109996 A1 | 5/2013 | Turnbull |
| 2013/0138010 A1 | 5/2013 | Nierenberg |
| 2013/0304407 A1 | 11/2013 | George |
| 2014/0121555 A1 | 5/2014 | Scott |
| 2014/0275926 A1 | 9/2014 | Scott |
| 2014/0276181 A1 | 9/2014 | Sun |
| 2015/0230749 A1 | 8/2015 | Gharib |
| 2015/0372433 A1 | 12/2015 | Lisogurski |
| 2016/0000382 A1 | 1/2016 | Jain |
| 2016/0174861 A1 | 6/2016 | Cadwell |
| 2016/0328991 A1 | 11/2016 | Simpson |
| 2018/0161123 A1 | 6/2018 | Cadwell |
| 2018/0198218 A1* | 7/2018 | Regan ................ H01R 9/2475 |
| 2019/0190187 A1* | 6/2019 | Fukazawa ............. H01R 24/84 |
| 2020/0330772 A1* | 10/2020 | Hartmann-Bax .. H01R 13/2492 |

FOREIGN PATENT DOCUMENTS

| | | |
|---|---|---|
| EP | 0863719 A1 | 9/1998 |
| EP | 890341 | 1/1999 |
| EP | 972538 | 1/2000 |
| EP | 1182965 B1 | 3/2002 |
| EP | 2173238 A2 | 4/2010 |
| WO | 2000038574 A1 | 7/2000 |
| WO | 2000066217 A1 | 11/2000 |
| WO | 2001037728 A1 | 5/2001 |
| WO | 2003005887 A2 | 1/2003 |
| WO | 2005030318 A1 | 4/2005 |
| WO | 2006042241 A2 | 4/2006 |
| WO | 2016028822 A1 | 2/2016 |

OTHER PUBLICATIONS

Clements, et. al., "Evoked and Spontaneous Electromyography to Evaluate Lumbosacral Pedicle Screw Placement", 21 (5):600-604 (1996).

Danesh-Clough, et. al., "The Use of Evoked EMG in Detecting Misplaced Thoracolumbar Pedicle Screws", 26(12):1313-1316 (2001).

Dezawa et al., "Retroperitoneal Laparoscopic Lateral Approach to the Lumbar Spine: A New Approach, Technique, and Clinical Trial", Journal of Spinal Disorders 13(2):138-143 (2000).

Dickman, et al., "Techniques in Neurosurgery", National Library of Medicine, 3 (4) 301-307 (1997).

Epstein, et al., "Evaluation of Intraoperative Somatosensory-Evoked Potential Monitoring During 100 Cervical Operations", 18(6):737-747 (1993), J.B. Lippincott Company.

Glassman, et. al., "A Prospective Analysis of Intraoperative Electromyographic Monitoring of Pedicle Screw Placement with Computed Tomography Scan Confirmation", 20(12):1375-1379.

Goldstein, et. al., "Minimally Invasive Endoscopic Surgery of the Lumbar Spine", Operative Techniques in Orthopaedics, 7 (1):27-35 (1997).

Greenblatt, et. al., "Needle Nerve Stimulator-Locator", 41 (5):599-602 (1962).

H.M. Mayer, "Minimally Invasive Spine Surgery, A Surgical Manual", Chapter 12, pp. 117-131 (2000).

Hinrichs, et al., "A trend-detection algorithm for intraoperative EEG monitoring", Med. Eng. Phys. 18 (8):626-631 (1996).

Bergey et al., "Endoscopic Lateral Transpsoas Approach to the Lumbar Spine", Spine 29 (15):1681-1688 (2004).

Holland, "Spine Update, Intraoperative Electromyography During Thoracolumbar Spinal Surgery", 23 (17):1915-1922 (1998).

Holland, et. al., "Continuous Electromyographic Monitoring to Detect Nerve Root Injury During Thoracolumbar Scoliosis Surgery", 22 (21):2547-2550 (1997), Lippincott-Raven Publishers.

Hovey, A Guide to Motor Nerve Monitoring, pp. 1-31 Mar. 20, 1998, The Magstim Company Limited.

Kevin T. Foley, et. al., "Microendoscipic Discectomy" Techniques in Neurosurgery, 3:(4):301-307, © 1997 Lippincott-Raven Publishers, Philadelphia.

Kossmann et al., "The use of a retractor system (SynFrame) for open, minimal invasive reconstruction of the anterior column of the thoracic and lumbar spine", 10:396-402 (2001).

Kossmann, et. al., "Minimally Invasive Vertebral Replacement with Cages in Thoracic and Lumbar Spine", European Journal of Trauma, 2001, No. 6, pp. 292-300.

Lenke, et. al., "Triggered Electromyographic Threshold for Accuracy of Pedicle Screw Placement, An Animal Model and Clinical Correlation", 20 (14):1585-1591 (1995).

Lomanto et al., "7th World Congress of Endoscopic Surgery" Singapore, Jun. 1-4, 2000 Monduzzi Editore S.p.A.; email: monduzzi@monduzzi.com, pp. 97-103 and 105-111.

MaGuire, et. al., "Evaluation of Intrapedicular Screw Position Using Intraoperative Evoked Electromyography", 20 (9):1068-1074 (1995).

(56) References Cited

OTHER PUBLICATIONS

Mathews et al., "Laparoscopic Discectomy With Anterior Lumbar Interbody Fusion, A Preliminary Review", 20 (16):1797-1802, (1995), Lippincott-Raven Publishers.
Bertagnoli, et. al., "The AnteroLateral transPsoatic Approach (ALPA), A New Technique for Implanting Prosthetic Disc-Nucleus Devices", 16 (4):398-404 (2003).
Michael R. Isley, et. al., "Recent Advances in Intraoperative Neuromonitoring of Spinal Cord Function: Pedicle Screw Stimulation Techniques", Am. J. End Technol. 37:93-126 (1997).
Minahan, et. al., "The Effect of Neuromuscular Blockade on Pedicle Screw Stimulation Thresholds" 25(19):2526-2530 (2000).
Pimenta et. al., "Implante de prótese de núcleo pulposo: análise inicial", J Bras Neurocirurg 12 (2):93-96, (2001).
Raymond J. Gardocki, MD, "Tubular diskectomy minimizes collateral damage", AAOS Now, Sep. 2009 Issue, http://www.aaos.org/news/aaosnow/sep09/clinical12.asp.
Raymond, et. al., "The NerveSeeker: A System for Automated Nerve Localization", Regional Anesthesia 17:151-162 (1992).
Reidy, et. al., "Evaluation of electromyographic monitoring during insertion of thoracic pedicle screws", British Editorial Society of Bone and Joint Surgery 83 (7):1009-1014, (2001).
Rose et al., "Persistently Electrified Pedicle Stimulation Instruments in Spinal Instrumentation: Technique and Protocol Development", Spine: 22(3): 334-343 (1997).
Teresa Riordan "Patents; A businessman invents a device to give laparoscopic surgeons a better view of their worK", New York Times www.nytimes.com/2004/29/business/patents-businessman-invents-device-give-la (Mar. 2004).
Toleikis, et. al., "The usefulness of Electrical Stimulation for Assessing Pedicle Screw Placements", Journal of Spinal Disorders, 13 (4):283-289 (2000).
U.Schick, et. al., "Microendoscopic lumbar discectomy versus open surgery: an intraoperative EMG study", pp. 20-26, Published online: Jul. 31, 2001 © Springer-Verlag 2001.
Bose, et. al., "Neurophysiologic Monitoring of Spinal Nerve Root Function During Instrumented Posterior Lumbar Spine Surgery", 27 (13):1440-1450 (2002).
Vaccaro, et. al., "Principles and Practice of Spine Surgery", Mosby, Inc. © 2003, Chapter 21, pp. 275-281.
Vincent C. Traynelis, "Spinal arthroplasty", Neurosurg Focus 13 (2):1-7. Article 10, (2002).
Welch, et. al., "Evaluation with evoked and spontaneous electromyography during lumbar instrumentation: a prospective study", J Neurosurg 87:397-402, (1997).
Zouridakis, et. al., "A Concise Guide to Intraoperative Monitoring", Library of Congress card No. 00-046750, Chapter 3, p. 21, chapter 4, p. 58 and chapter 7 pp. 119-120.
Medtronic, "Nerve Integrity Monitor, Intraoperative EMG Monitor, User's Guide", Medtronic Xomed U.K. Ltd., Unit 5, West Point Row, Great Park Road, Almondsbury, Bristol B5324QG, England, pp. 1-39.
Chapter 9, "Root Finding and Nonlinear Sets of Equations", Chapter 9:350-354, http://www.nr.com.
Digitimer Ltd., 37 Hydeway, Welwyn Garden City, Hertfordshire. AL7 3BE England, email:sales@digitimer.com, website: www.digitimer.com, "Constant Current High Voltage Stimulator, Model DS7A, For Percutaneous Stimulation of Nerve and Muscle Tissue".
Ford et al, Electrical characteristics of peripheral nerve stimulators, implications for nerve localization, Dept. of Anesthesia, University of Cincinnati College of Medicine, Cincinnati, OH 45267, pp. 73-77.
Deletis et al, "The role of intraoperative neurophysiology in the protection or documentation of surgically induced injury to the spinal cord", Correspondence Address: Hyman Newman Institute for Neurology & Neurosurgery, Beth Israel Medical Center, 170 East End Ave., Room 311, NY 10128.
Urmey "Using the nerve stimulator for peripheral or plexus nerve blocks" Minerva Anesthesiology 2006; 72:467-71.
Butterworth et. al., "Effects of Halothane and Enflurane on Firing Threshold of Frog Myelinated Axon", Journal of Physiology 411:493-516, (1989) From the Anesthesia Research Labs, Brigham and Women's Hospital, Harvard Medical School, 75 Francis St., Boston, MA 02115, jp.physoc.org.
Calancie, et. al., "Threshold-level multipulse transcranial electrical stimulation of motor cortex for intraoperative monitoring of spinal motor tracts: description of method and comparison to somatosensory evoked potential monitoring" J Neurosurg 88:457-470 (1998).
Calancie, et. al., "Threshold-level repetitive transcranial electrical stimulation for intraoperative monitoring of central motor conduction", J. Neurosurg 95:161-168 (2001).
Calancie, et. al., Stimulus-Evoked EMG Monitoring During Transpedicular Lumbosacral Spine Instrumentation, Initial Clinical Results, 19 (24):2780-2786 (1994).
Carl T. Brighton, "Clinical Orthopaedics and Related Research", Clinical Orthopaedics and related research No. 384, pp. 82-100 (2001).
International Search Report for PCT/US2019/063793, dated Feb. 19, 2020.
International Search Report for PCT/US2017/062559, dated Jan. 26, 2018.

* cited by examiner

CONNECTOR RECEPTACLE

CROSS-REFERENCE

The present application relies on U.S. Patent Provisional Application No. 62/794,884, entitled "Connector Receptacle" and filed on Jan. 21, 2019, for priority, which is herein incorporated by reference in its entirety.

FIELD

The present specification generally relates to female DIN receptacles, and particularly to a resilient circular female DIN receptacle configured to maintain mating retention and withstand a high number of mating cycles.

BACKGROUND

Electrophysiological methods, such as electroencephalography (EEG), electromyography (EMG), and evoked potentials, measure the functional integrity of certain neural structures (e.g., nerves, spinal cord and parts of the brain). Neurodiagnostics is the use of electrophysiological methods, such as electroencephalography (EEG), electromyography (EMG), and evoked potentials (EP), to diagnose the functional integrity of certain neural structures (e.g., nerves, spinal cord and parts of the brain) to assess disease states and determine potential therapy or treatment. With EMG and EPs, a neurologist typically utilizes electrodes applied to the patient near the nerves being assessed. These electrodes used are in many forms including needles, metal disks, and conductive pads. Each of these electrodes is coupled to a wire lead which, in turn, is connected to an amplifier for amplification of the EMG or EP electrical signals. The wire leads are usually coupled with standard connectors comprising a male plug which fits into a corresponding female receptacle for connecting with the control unit of monitoring equipment, such as, for example, EMG monitoring equipment. The electrical activity pattern captured by various electrodes is analyzed using standard algorithms to localize or spot the portion of brain which is responsible for causing the specific ailment.

During a typical EMG and EP study, the electrodes are connected and disconnected many times, thus requiring a connector that can withstand many mating cycles. After many mating cycles, the connector must maintain reliable electrical connectivity and mating force. An appropriate mating force is necessary since a low mating force may result in the connector being pulled out of the amplifier during the EMG or EP study.

The standard Deutsches Institut für Normung (DIN) connector, for example, a 45322 DIN connector (5 position circular), is a default standard connector used in EMG equipment. Both recording and stimulating electrodes may terminate with male DIN connector plugs. During the course of a patient examination, the connector may be mated/unmated multiple times. The number of mating cycles on a daily basis may exceed 20 depending on the application. Commercially available circular female DIN connector receptacles are typically rated for 1000 mating cycles.

Current methods of securing a DIN connector are not suitable for use with an EMG or EP instrument. These methods include spring fingers and some sort of latching mechanism. Spring fingers have limited mating cycles below what is required for EMG/EP instruments. Latching mechanisms for DIN connectors are not desirable for the following reasons: requires a non-standard DIN plug that would limit the possibility of available electrodes, add cost to the electrode, and require more effort, such as twisting or pressing, to remove the DIN plug from the amplifier.

FIG. 1A illustrates a standard prior art circular male DIN plug, such as a male DIN 45322 plug. FIG. 1B illustrates a prior art female DIN receptacle for the male DIN plug shown in FIG. 1A. In order to enable connection, male DIN plug 102 and female DIN receptacle 104 are mated by fitting the male DIN plug 102 into female DIN receptacle 104. Removing the male DIN plug 102 from the female DIN receptacle 104 results in un-mating or breaking the connection. Beyond 1000 cycles of mating/un-mating, the female DIN receptacle 104 may experience poor electrical contact and retention force of the male DIN connector plug 102.

The retention force of commercially available DIN receptacles relies on the friction between the DIN plug prong and the DIN receptacle pin socket. One type of pin socket is tulip shaped. The poor retention force is due to an elasticity and/or mechanical breakdown of the tulip shaped contacts 106 in the female DIN receptacle 104. The tulip shaped contacts 106 are subject to distortion after repeated mating cycles. Thus, for a female DIN receptacle that is rated for 1000 cycles, the receptacle starts losing its electric contact and retention force after 50 days of use in EMG equipment. Another type of pin socket is a circular contact. Certain variations of the circular contact have superior electrical contact with high mating cycles. However, the retention force of the circular contact is low. Low retention force of the female DIN receptacle is problematic since the electrode may disconnect from the EMG equipment as the electrode is moved about the patient during the examination.

FIG. 1C illustrates a plurality of standard prior art circular female DIN receptacles. FIG. 1C depicts:

A first female DIN receptacle 110, also referred to as a DIN 41524 receptacle, having three contacts 111, each configured to receive a pin;

A second female DIN receptacle 112 having four contacts 113, each configured to receive a pin;

A third female DIN receptacle 114, also referred to as a DIN 45327 receptacle, having five contacts 115, each configured to receive a pin and further configured with a central contact surrounded by four equidistant contacts;

A fourth female DIN receptacle 116, also referred to as a DIN 45322, having five contacts 115, each configured to receive a pin and further configured with a central contact positioned between two right and two left contacts placed in parallel;

A fifth female DIN receptacle 118, also referred to as a DIN 41524 receptacle, having five contacts 115, each configured to receive a pin and further configured in an arc;

A sixth female DIN receptacle 120, also referred to as a DIN 45522 receptacle, having six contacts 121, each configured to receive a pin;

A seventh female DIN receptacle 122, also referred to as a DIN 45329 receptacle, having seven contacts 123;

An eighth female DIN receptacle 124, also referred to as a DIN 45326 receptacle, having eight contacts 125 as shown in FIG. 1C; and A ninth female DIN receptacle 126 having eight contacts 125 as shown in FIG. 1C.

U.S. Pat. No. 4,284,313, assigned to ITT Corporation, discloses a detachable electrical connector in which "a resilient hood on the receptacle connector member surrounds the forward portion of the plug connector member. Lugs on the plug connector member snap into recesses in the hood to latch the connector members together. The hood is connected to the body of the receptacle member by longitudinally extending ribs. In one embodiment of the invention, the hood is circular and is rotated to ride up over the latching lugs to release the lugs from the recesses, thereby allowing the connector members to be disengaged."

U.S. Pat. No. 4,842,555, assigned to AMP Incorporated, discloses a surface mounted electrical connector which "has a metal shield (12) having a front plate (28) with a circular opening (30) for receiving a shielded socket (18) of a mating connector (20), to allow it to mate with a plug portion (16) of the surface mounted connector (10). Spring fingers (34) project from the edge (32) of the opening (30) for engaging shielding (19) of the mating connector (20). Between a pair of the fingers (34) there also projects form the edge (32), a latching finger (80) which is shorter than the spring fingers (34), for latching behind a depressable protuberance (90) on the socket (18). When the plug portion (16) is to be mated with the socket (18), a flexible arm (98) in the socket (18), which carries the protuberance (90) is supported by a support bar (88) which is stiffly resilient. During mating, the protuberance (90) displaces the latching finger (80) and latches behind its free end (84). A sleeve (100) on the mating connector (20) can be pulled to withdraw the support bar (98) so that the protuberance can slide under the latching finger (80) to allow the connectors (10 and 20) to be unmated."

U.S. Pat. No. 5,035,650, assigned to AMP Incorporated, discloses "a dielectric housing (4) of a circular, shielded DIN electrical connector (2) [which] comprises a central block (26) with terminal receiving cavities (18) extending axially therethrough and which cooperates with a hood (30) and a base (28) of the housing (4) to define a circular chamber receiving a circular, stamped and formed metal shield (8). The shield (8) has projecting therefrom a uniplanar latch arm (80) having a head (81) which latches positively against a latching shoulder (88) in a slot in the base. The latch arm (80) is deflected in its own plane by a cam surface in the slot as the latch arm (80) is inserted thereinto and then resiles to allow the head (81) to latch against the shoulder (88)."

U.S. Pat. No. 5,871,371, assigned to The Whitaker Corporation, discloses "an electrical connector for providing connection for a plurality of coaxial cable disposed in a shielded cable. The connector includes a contact housing having a plurality of signal and ground contacts mounted therein. The contact housing has an outer periphery. The signal and ground contacts are disposed about the outer periphery of the contact housing. The signal and ground contacts each have contact sections and connection sections for forming an electrical connection with the signal and ground from a coaxial cable."

U.S. Pat. No. 6,183,293, assigned to ITT Manufacturing, Inc., discloses an "electrical connector for mounting in an opening (2) of a wall (3), [which] includes a connector element (4) having a bayonet threaded shaft (7) that projects into the opening and a clamp element (5) with a nut part that can be threaded onto the threaded shaft until shoulders on the two elements abut the wall, where the connector includes a latching mechanism (40) that prevents loosening of the clamp member. The latching mechanism includes a holder ring (54) on the connector element, that lies within a latch ring (50) on the clamp element. The latch ring has inwardly-extending projections (42, 44), while the holder ring carries at least one latch member (14). When the clamping member is tightened on the connector element, the distal end (15a) of the latch member readily rides over the projections. However, when the clamping member begins to loosen, the distal end resists such loosening."

U.S. Pat. No. 9,088,103, assigned to Omnetics Connector Corporation, discloses an "apparatus and system for securing a mated connector pair with a latch. The latch is a unitary elongate body configured to receive the mated connector pair. The latch may include a spring member and an internal passageway configured to receive a miniature circular connector. The latch may include a wire retainer feature to secure the latch to a wire harness."

The prior art does not address the need for greater retention force between the plug and receptacle of a DIN connector without the use of a latching mechanism. The prior art also does not provide a DIN connector that does not deteriorate by repeated mating cycles of its plug and receptacle.

Hence, there is a need for a DIN connector receptacle with an improved rating of multiples of 1000 cycles, which is compatible with the standard DIN connector plug to consistently provide a reliable connection over thousands of uses. There is also a need for an improved DIN receptacle which is not worn out by repeated mating and un-mating cycles and is corrosion resistant. Since receptacles comprising spring leaf type clips tend to flatten out after repeated cycles, which results in loss of retention force, there is also a need for a receptacle design which would support multiple mating cycles without loss of retention with standard DIN plugs and with no cost increase for the DIN plug.

SUMMARY

The following embodiments and aspects thereof are described and illustrated in conjunction with systems, tools and methods, which are meant to be exemplary and illustrative, not limiting in scope.

In some embodiments, the present specification discloses a receptacle configured to receive a plug comprising a plurality of pins, wherein the receptacle comprises a first housing having a circular enclosure wall defined by an exterior surface and an interior surface, wherein the interior surface of the enclosure wall encircles an interior space of the first housing, wherein the circular enclosure wall comprises at least one cavity; a plug receiver having an exterior surface and positioned within the interior space of the first housing, wherein the interior surface of the wall circumferentially surrounds the exterior surface of the plug receiver and is separated from the exterior surface of the plug receiver by a circular gap, and wherein the plug receiver comprises a plurality of connectors each configured to receive one of the plurality of pins of the plug; a first protrusion member positioned in the at least one cavity within the circular enclosure wall; and a retention band circumferentially positioned around the interior space and in physical communication with the circular enclosure wall, wherein the retention band is configured to physically force the first protrusion member out of the at least one cavity and into the circular gap.

Optionally, the first protrusion member is a ball bearing.

Optionally, the retention band is positioned within a groove extending circumferentially around the interior surface of the enclosure wall.

Optionally, the receptacle is a female DIN connector receptacle.

Optionally, the plug is a male DIN connector plug.

Optionally, the first protrusion member is a ball bearing and wherein the ball bearing is made of stainless steel.

Optionally, the receptacle is configured to connect EMG electrodes with an EMG control system via an amplifier.

Optionally, the at least one cavity comprises a first cavity and a second cavity and further comprising a second protrusion member positioned in the second cavity, separate and distinct from the first cavity, within the circular enclosure wall.

Optionally, the retention band is configured to physically force the second protrusion member out of the second cavity and further into the circular gap.

Optionally, the first protrusion member and the second protrusion member are positioned 180 degrees from each other on opposite sides of the circular enclosure wall.

Optionally, the first protrusion member is a ball bearing, the second protrusion member is a ball bearing, and both the first protrusion member and second protrusion member are configured to be pressed against an outside surface of the plug by a spring force provided by the retention band.

Optionally, the first housing and the plug receptacle are molded.

Optionally, the retention band is an O-ring having a durometer rating in a range of 50 to 90 Shore.

Optionally, the receptacle further comprises a second protrusion member positioned in a second cavity, separate and distinct from the at least one cavity, within the circular enclosure wall and a third protrusion member positioned in a third cavity, separate and distinct from the second cavity and the at least one cavity, within the circular enclosure wall.

Optionally, the retention band is an O-ring having a durometer rating in a range of 50 to 90 Shore.

Optionally, the retention band is configured to physically force the second protrusion member out of the second cavity and further into the circular gap and to physically force the third protrusion member out of the third cavity and further into the circular gap.

Optionally, the first protrusion member, the second protrusion member, and the third protrusion member are positioned 120 degrees from each other circumferentially around the circular enclosure wall.

In some embodiments, the present specification discloses a female receptacle configured to connect to a male plug, wherein the female receptacle comprises a first circular housing circumferentially surrounding a plug receptacle, wherein an internal surface of the first circular housing is separated from the plug receptacle by a circular gap and wherein the plug receptacle comprises a plurality of hollow connector spaces each configured to receive a pin of the male plug, the female receptacle further comprising: a first state wherein a first protrusion member is configured to be positioned in a first cavity within the first circular housing and a retention band is configured to be circumferentially positioned around a surface of the first circular housing and physically force the first protrusion member out of the first cavity and further into the circular gap by a first distance; and a second state wherein the first protrusion member is configured to be positioned in the first cavity within the first circular housing and the retention band is configured to be circumferentially positioned around the surface of the first circular housing and physically force the first protrusion member out of the first cavity and further into the circular gap by a second distance, wherein the second distance is less than the first distance and wherein the second state is achieved by inserting the male plug into the female receptacle.

Optionally, the first protrusion member is a ball bearing.

Optionally, the female receptacle further comprises a second cavity, separate and distinct from the first cavity, in the first circular housing and a second protrusion member positioned in the second cavity within the circular enclosure wall.

Optionally, the retention band is configured to physically force the second protrusion member out of the second cavity and further into the circular gap.

In some embodiments, the present specification discloses a connector receptacle for connecting with a corresponding connector plug coupled with electrodes being used for performing EMG procedure on a patient, the receptacle comprising: a first ball bearing pressing against a first end of a housing of the plug and a second ball bearing pressing against a first end of the housing of the plug when the plug is connected to the receptacle for exerting a retention force against the plug, wherein the first and the second ball bearings are pressed against the first and the second ends respectively by using a spring force.

Optionally, the connector receptacle comprises a high mating cycle circular DIN connector receptacle.

Optionally, said receptacle is compatible with a DIN connector plug.

Optionally, the first and the second ball bearings are made of stainless steel.

Optionally, the spring force is provided by at least one retention band.

Optionally, the retention band comprises a high durometer and low compression set O-ring.

Optionally, the retention band exerts a compression force against the first and the second ball bearings, the compression force being transmitted to the housing of the plug for retaining the plug within the receptacle.

Optionally, the spring force is provided by using a circular spring.

Optionally, the spring force is provided by wounding a circular spring around a center portion of the receptacle for pushing the first and the second ball bearings against the housing of the plug.

Optionally, the spring force is provided by using a coiled spring to push the ball bearings inwards towards the housing of the plug when the plug is connected to the receptacle.

Optionally, the receptacle comprises a molded enclosure encompassing a housing of the receptacle.

The aforementioned and other embodiments of the present specification shall be described in greater depth in the drawings and detailed description provided below.

BRIEF DESCRIPTION OF THE DRAWINGS

These and other features and advantages of the present specification will be appreciated, as they become better understood by reference to the following detailed description when considered in connection with the accompanying drawings, wherein.

DETAILED DESCRIPTION

In an embodiment, the present specification provides a high mating cycle circular female DIN connector receptacle. In some embodiments, the circular female DIN receptacle comprises one or more curved or beveled components which press against a housing hood of a corresponding compatible male DIN plug, generating friction for obtaining a greater retention force than that demonstrated by the prior art DIN connectors/receptacles. In various embodiments, the curved or beveled components comprise stainless steel ball bearings. The greater retention force inhibits premature disengagement between a male DIN plug and female DIN receptacle.

In embodiments, the female DIN receptacle of the present specification can be used with any standard male DIN connector and is compatible with standardized male DIN plugs. In an embodiment, the female DIN receptacle of the present specification is used in amplifiers (2 and 12 channels) being used in conjunction with EMG equipment.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention. In the description and claims of the application, each of the words "comprise" "include" and "have", and forms thereof, are not necessarily limited to members in a list with which the words may be associated.

It should be noted herein that any feature or component described in association with a specific embodiment may be used and implemented with any other embodiment unless clearly indicated otherwise.

Figure 1A:
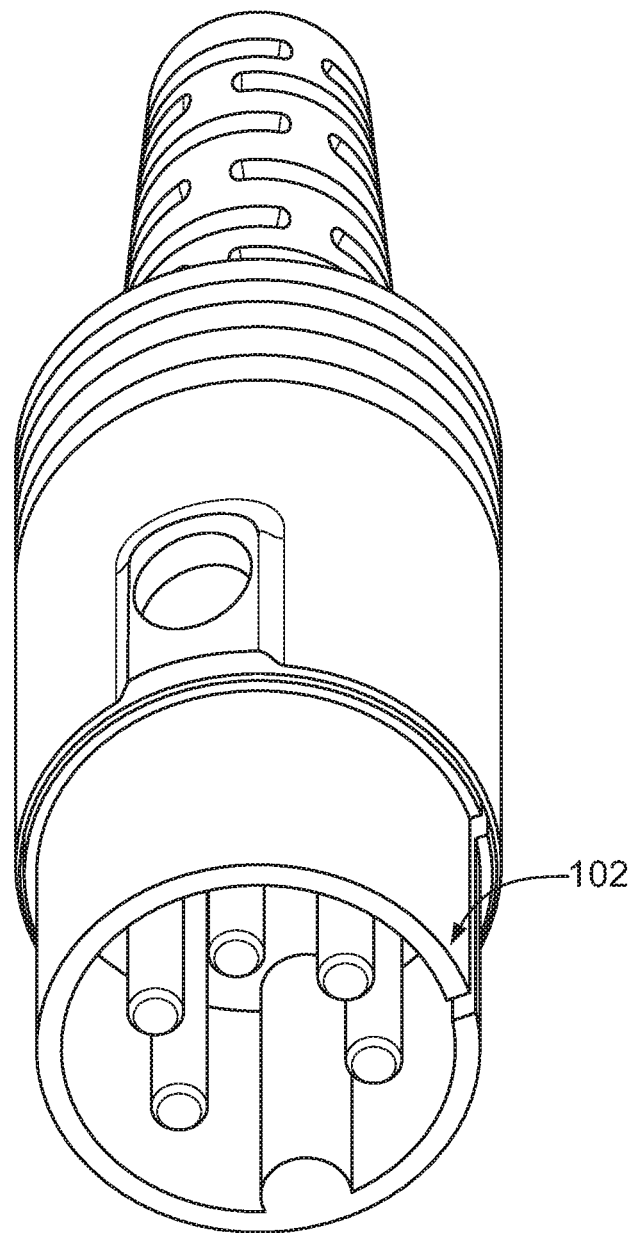
FIG. 1A illustrates a standard prior art male DIN plug.
Figure 1B:
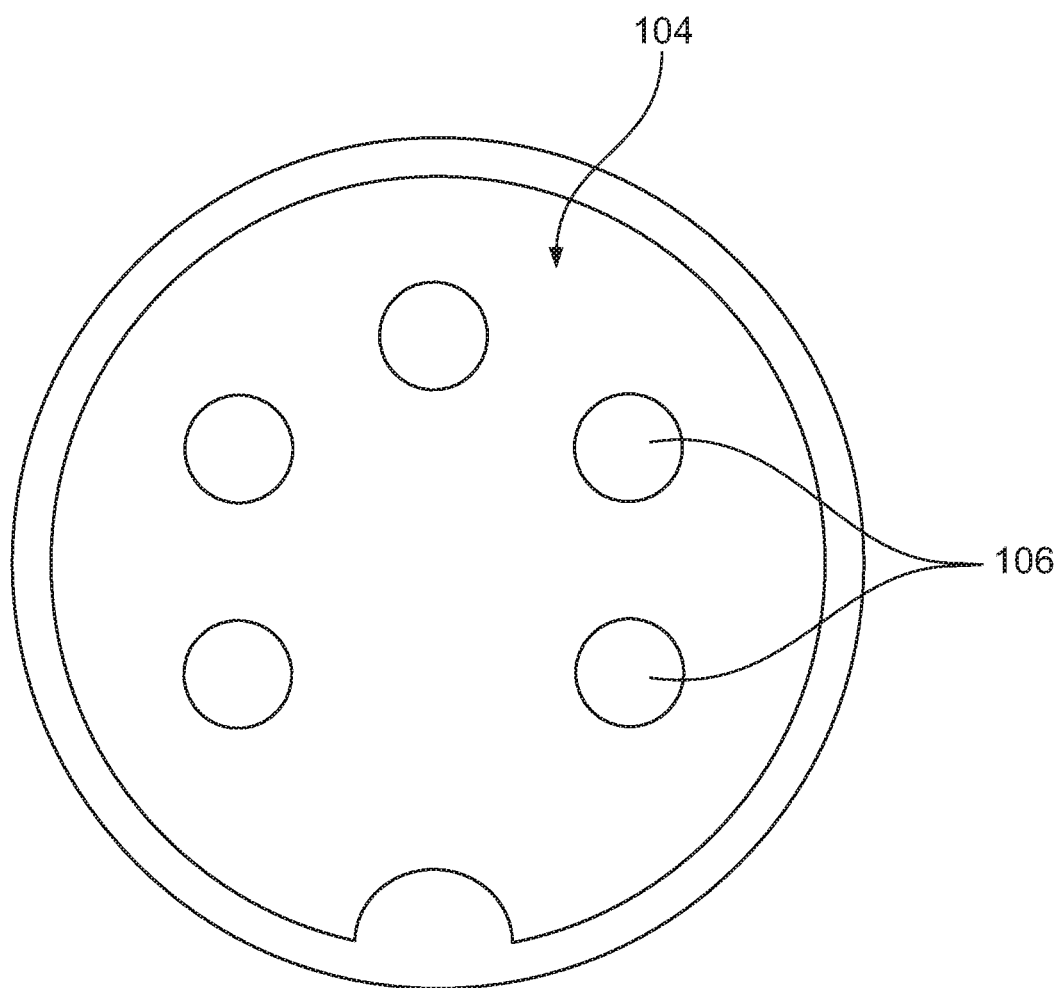
FIG. 1B illustrates a prior art female DIN receptacle for the male DIN plug shown in FIG. 1A.
Figure 1C:
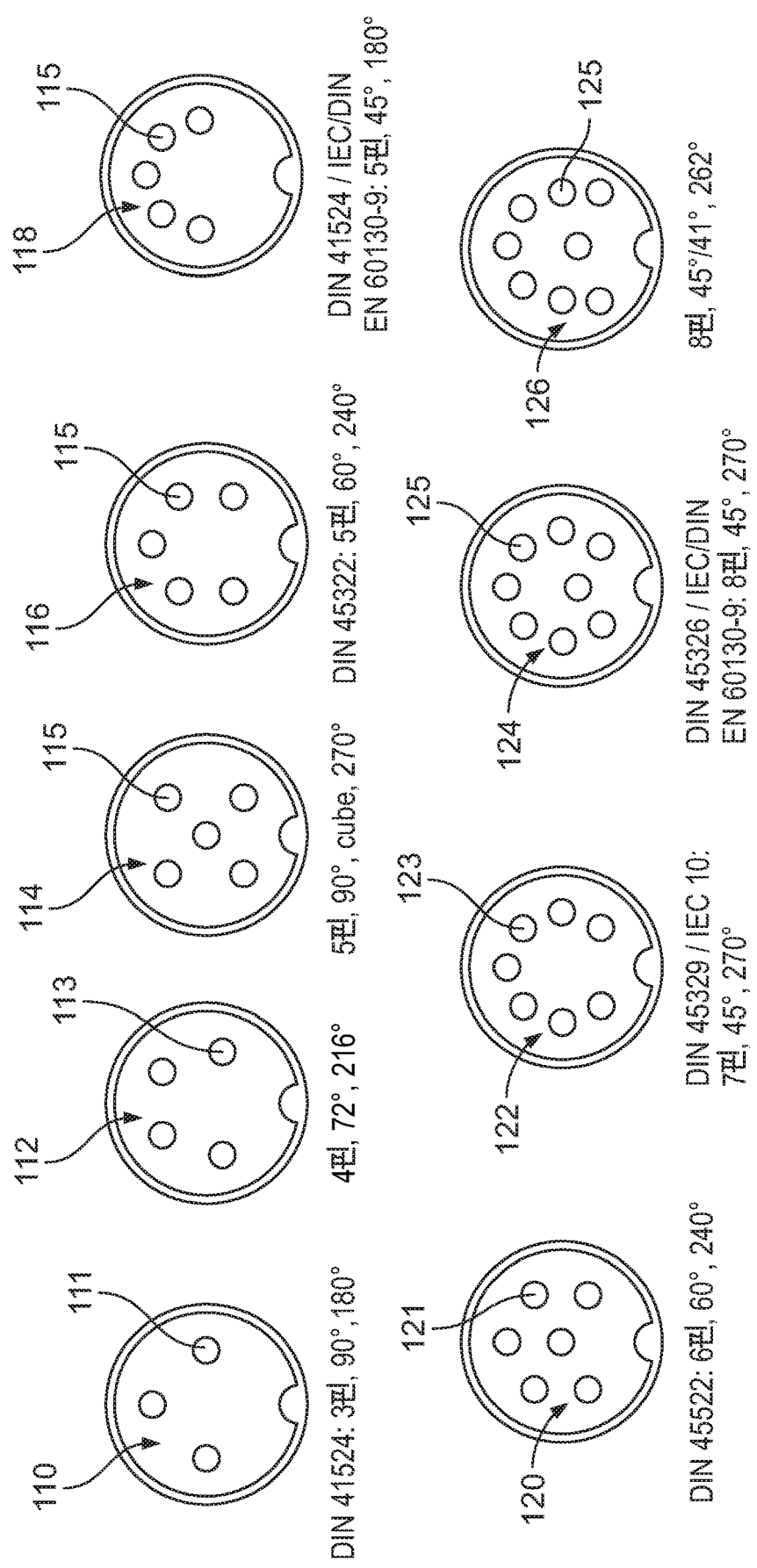
FIG. 1C illustrates a plurality of standard prior art circular female DIN receptacles.
Figure 2A:
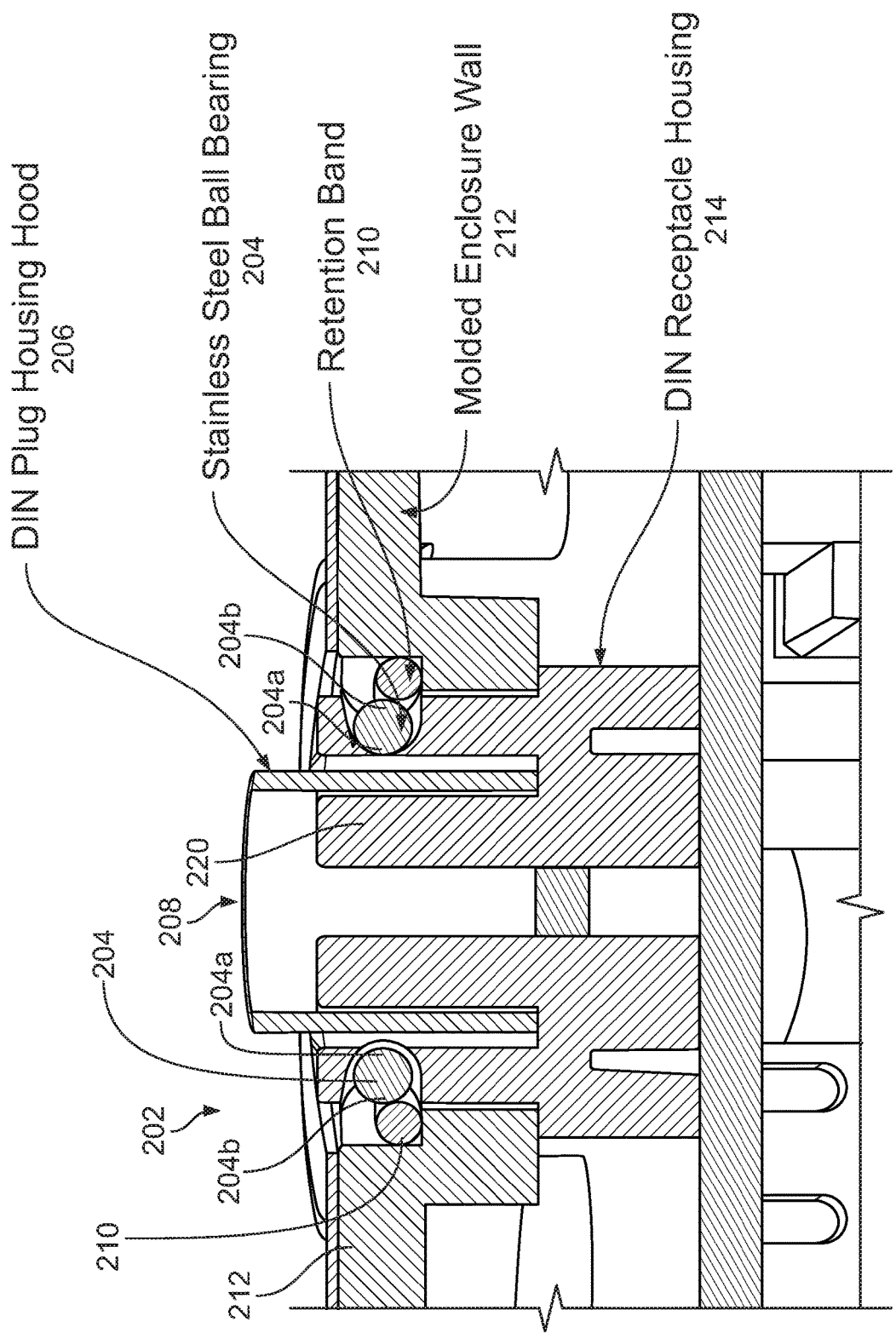
FIG. 2A illustrates a cross sectional diagram of a female DIN receptacle coupled with a corresponding male DIN plug, in accordance with an embodiment of the present specification.
Figure 2B:
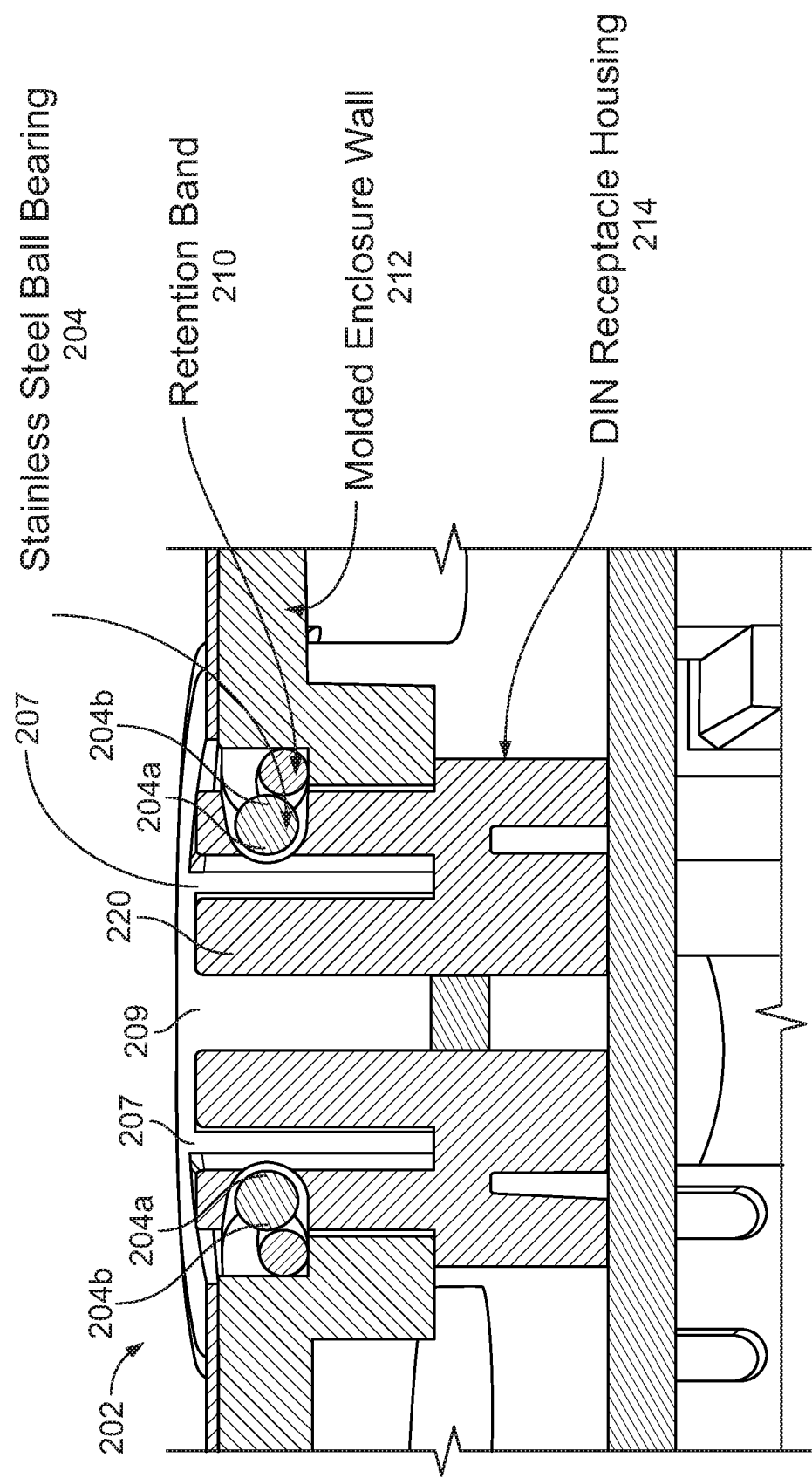
FIG. 2B illustrates a cross sectional diagram of the female DIN receptacle of FIG. 2A without the male DIN plug, in accordance with an embodiment of the present specification.
Figure 2C:
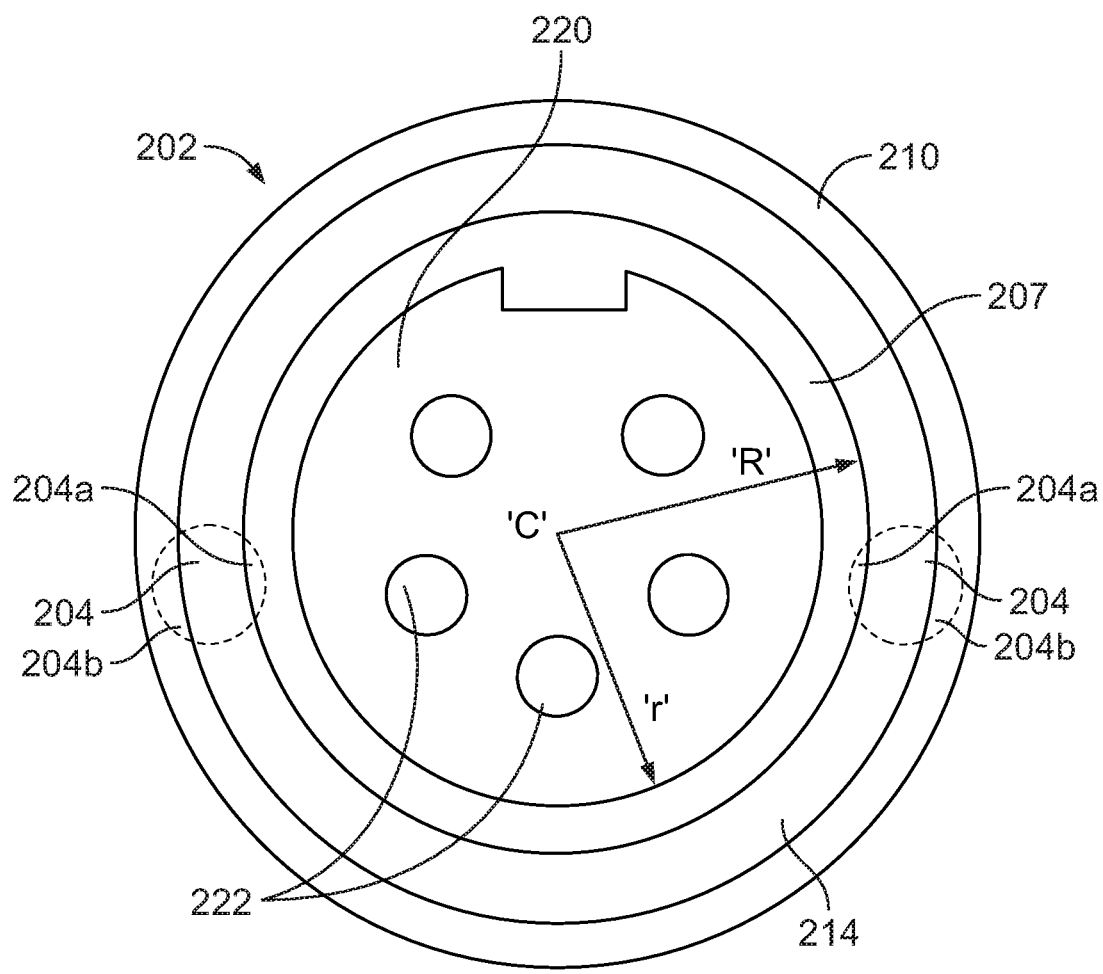
FIG. 2C is a top view cross sectional diagrammatical representation of the female DIN receptacle of FIG. 2B.

FIG. 2A illustrates a cross sectional diagram of a female DIN connector receptacle 202 coupled with a corresponding male DIN plug 208, in accordance with an embodiment of the present specification. FIG. 2B illustrates a cross sectional diagram of the female DIN connector receptacle 202 of FIG. 2A without the male DIN plug 208, in accordance with an embodiment of the present specification. FIG. 2C is a top view cross sectional diagrammatical representation of the female DIN receptacle of FIG. 2B.

Referring to FIGS. 2A, 2B and 2C, the female DIN receptacle 202 comprises a circular housing 214 circumferentially surrounding a plug receptacle 220. The plug receptacle 220 comprises a plurality of connectors 222 each of which is configured to receive a corresponding pin of the male DIN plug 208. In embodiments, an internal surface of the circular housing 214 is separated from the plug receptacle 220 by a circular gap, well or cavity 207. In some embodiments, the circular housing and the plug receptacle are molded such that they are connected with a gap incorporated therein, as described above.

In some embodiments, the female DIN receptacle 202 further comprises first and second protrusion members 204 positioned, respectively, in first and second gaps, spaces or notches within the circular housing 214. In some embodiments, the first and second protrusion members 204 are positioned 180 degrees from each other (that is, diametrically opposite) around the circular housing 214. In some embodiments, the first protrusion member is a ball bearing. In some embodiments, the first and second protrusion members 204 are ball bearings.

As shown in FIGS. 2A, 2B and 2C, in some embodiments, the first and second protrusion members 204 are ball bearings which press against a housing hood 206 of the corresponding male DIN plug 208, from two opposing sides, when the male DIN plug 208 and the female DIN receptacle 202 are mated. While two ball bearings 204 are depicted in FIG. 2A, one or more ball bearings, such as 2, 3, 4, 5, 6, 7, 8 or more distributed evenly around the circular housing 214 of the female DIN receptacle 202, may be used in various embodiments of the present specification. In an embodiment, the ball bearings 204 are made out of stainless steel. In other embodiments, ball bearings of other suitable materials may also be used such as, but not limited to, chrome steel and ceramic (silicon nitride ($Si_3N_4$)).

In various embodiments, the ball bearings 204 are pressed against the housing hood 206 by using a spring force. Referring to FIG. 2B, the housing hood (206 of FIG. 2A) of the male DIN plug 208 is inserted into the circular gap 207 for mating/connecting with the female DIN receptacle 202. Also depicted is an opening 209 in the female DIN receptacle 202 for receiving a prong of the male DIN plug 208.

In an embodiment, the spring force is achieved by using a circular retention band or an elastomeric O-ring 210, wherein the retention band 210 presses against each of the ball bearings 204. The circular retention band 210 is circumferentially positioned around an outside surface of the circular housing 214. The retention band 210 is configured to physically force the first and second protrusion members 204 out of their respective first and second gaps and further into the circular gap 207. In some embodiments, when the male DIN plug 208 is not inserted into the female DIN receptacle 202, both the first and second protrusion members 204 are configured to be pressed against an outside surface of the plug receptacle 220 by the spring force provided by the retention band 210. In some embodiments, when the male DIN plug 208 is inserted into the female DIN receptacle 202, both the first and second protrusion members 204 are configured to be pressed against a surface of the male DIN plug 208, such as the housing hood 206, by the spring force provided by the retention band 210.

As can be seen in FIGS. 2A, 2B and 2C, the ball bearings 204 contact the retention band 210 on one end and extend into the gap 207 on the other end to contact the housing hood 206 of the male DIN plug 208 (once inserted) for a secure fit. A first portion 204a of the ball bearings 204 extends into the gap 207 to contact the housing hood 206 of the connector plug 208 when inserted, while a second portion 204b of the ball bearings, opposite the first portion 204a, contacts the compressible retention band 210. When the housing hood 206 of the male DIN plug 208 is inserted into the female DIN receptacle 202, the elastomeric retention band 210 applies pressure to the second portion 204b of the ball bearings, causing the ball bearings to move laterally such that the first portion 204a of the ball bearings contacts and applies a force to the housing hood 206, providing a more secure connection between the male DIN plug 208 and female DIN receptacle 202.

As shown in FIG. 2C, the circular gap 207 has an outer radius 'R' and an inner radius 'r' such that a width 'w' of the circular gap 207 is 'R-r'. In embodiments, the female DIN receptacle 202 has a first state and a second state. In the first state, the ball bearings 204 are positioned within the circular gap 207 such that X % of the width 'w' of the circular gap 207 comprises a ball bearing. In the second state, the ball bearings 204 are positioned within the circular gap 207 such that Y % of the width 'w' of the circular gap 207 comprises a ball bearing. In embodiments, Y % is less than X % when the first state corresponds to the male DIN plug 208 not being inserted into the female DIN receptacle 202 whereas the second state corresponds to the housing hood 206 of the male DIN plug 208 being inserted into the female DIN receptacle 202. Thus, in the first state the ball bearings are skewed radially towards a center 'C' of the female DIN receptacle 202 (as a result of being pushed by the retention band 210) causing the ball bearings to occupy a higher percentage (X %) of the width 'w' of the circular gap 207. However, in the second state the ball bearings are pushed radially away from the center 'C', by the inserted hood 206, against the retention band 210 causing the ball bearings to occupy a lesser percentage (Y %) of the width 'w' of the circular gap 207.

Stated differently, in the first state, the retention band 210 physically forces the first and second protrusion members 204 out of the respective first and second gaps and further into the circular gap 207 by a first distance. In the second state the retention band 210 physically force the first and second protrusion members 204 out of the respective first and second gaps and further into the circular gap 207 by a second distance. The second distance is less than the first distance when the second state is achieved by the male DIN plug 208 being inserted into the female DIN receptacle 202.

In some embodiments, the retention band 210 has a durometer rating in a range of 50-90 Shore. In an embodiment, the retention band 210 is a high durometer and low compression set O-ring for providing the spring force for pressing the ball bearings 204 against the housing hood 206 of the male DIN plug 208. The retention band 210 is placed in close contact with a ball bearing 204 in order to enable the retention band to press against the ball bearing, thereby creating friction and generating a large retention force between the male DIN plug 208 and the receptacle 202. In some embodiments, approximately 3.68 lbs of force is required to remove a seated male DIN plug 208 from the female DIN receptacle 202, compared to approximately 1.96 lbs of force in the prior art. In some embodiments, a range of 2 lbs or more of force, 2 lbs to 4 lbs of force, or 2 lbs to 5 lbs or force is required to remove a seated male DIN plug 208 from the female DIN receptacle 202, compared to approximately 1.96 lbs of force in the prior art. The retention band 210 is contained within a molded enclosure wall 212 of the female DIN receptacle 202, which also encloses a housing 214 of the female DIN receptacle 202, in order to further enable the retention band 210 to exert a compression force rather than being allowed to expand as the ball bearings 204 are forced out of the gap 207 by the male DIN plug housing hood 206 during disconnection/un-mating.

In another embodiment, a circular spring may be used to generate friction between the ball bearings 204 and the male DIN plug housing hood 206. The circular spring wraps around a center portion or plug receptacle 220 of the female DIN receptacle 202 and presses the ball bearing inward. In other words, a spring force is provided by wounding a circular spring around the center portion or plug receptacle 220 of the female DIN receptacle 202 for pushing the first and the second ball bearings 204 against the housing of the male DIN plug 208. In yet another embodiment, a coiled spring may be used to directly push the ball bearings 204 inward, for generating a retention force between the female DIN receptacle 202 and the male DIN plug 208. Thus, in this embodiment, a spring force is provided by using a coiled spring to push the ball bearings 204 inwards towards the housing of the male DIN plug 208 when the male DIN plug 208 is connected to the female DIN receptacle 202.

Figure 3A:
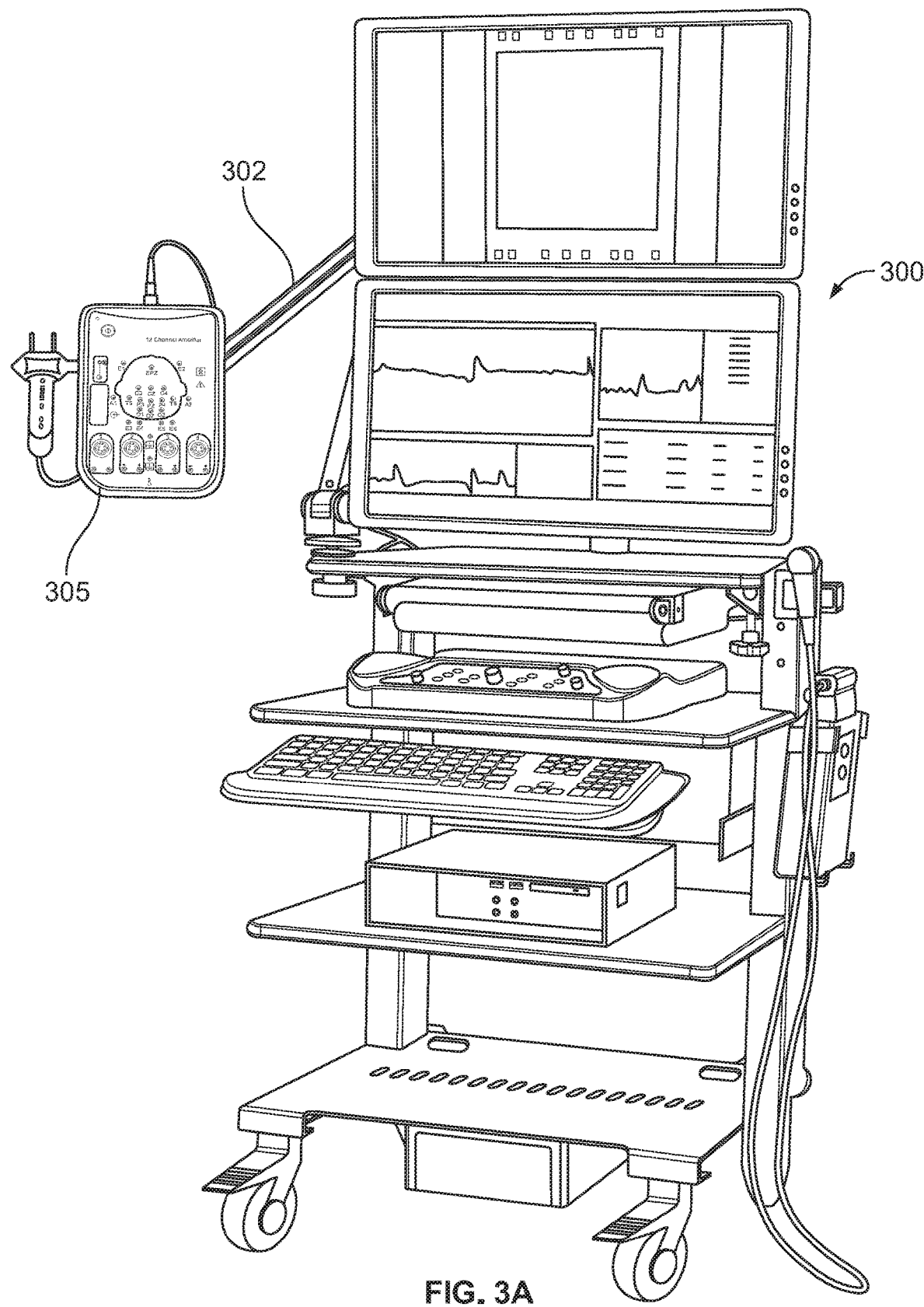
FIG. 3A illustrates equipment comprising an amplifier for performing an EMG procedure on a patient.
Figure 3B:
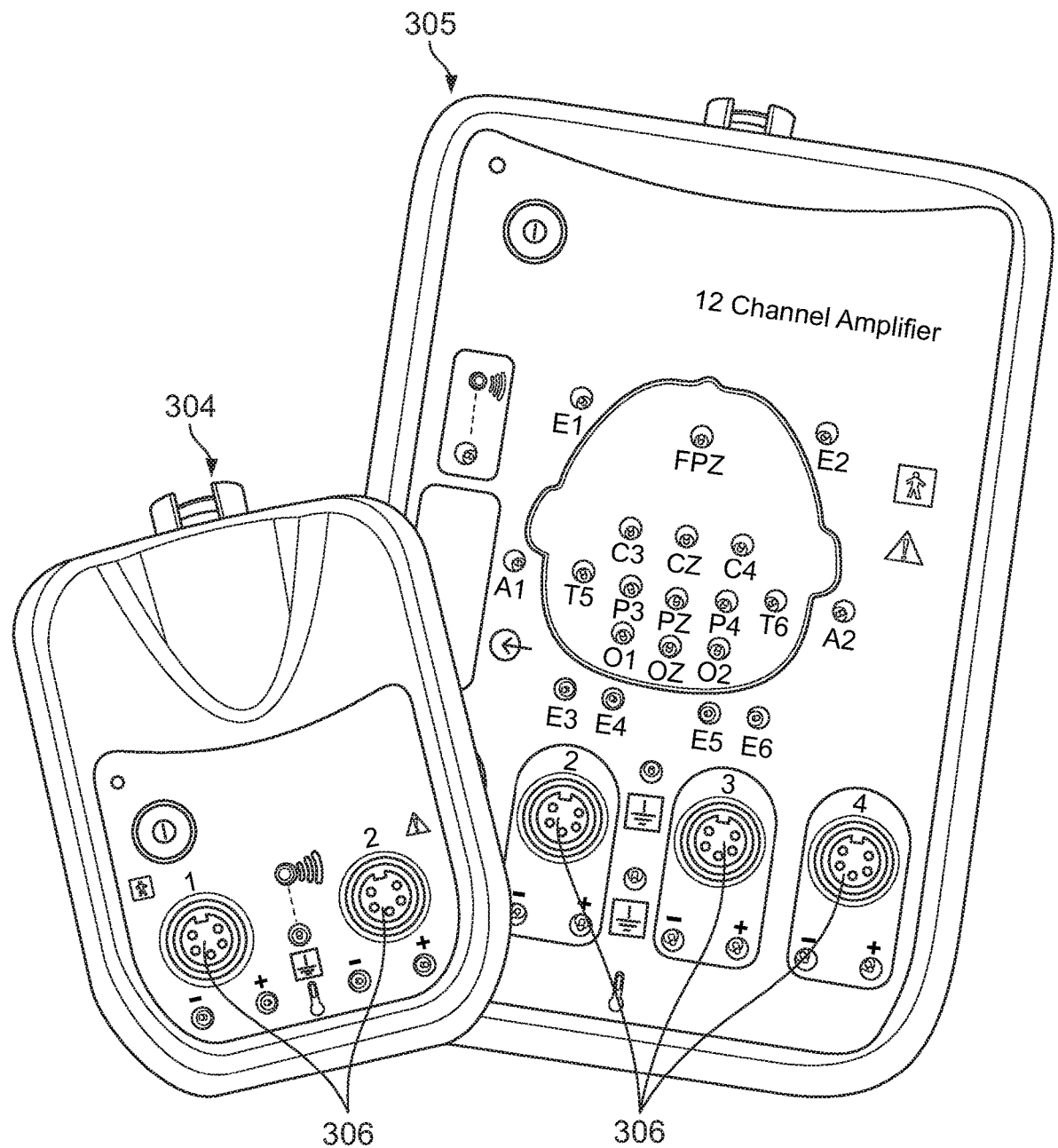
FIG. 3B illustrates amplifiers comprising female DIN receptacles, in accordance with an embodiment of the present specification.

FIG. 3A illustrates an equipment cart 300 comprising an amplifier 305 for performing an EMG procedure on a patient. FIG. 3B illustrates amplifiers 304, 305 comprising female DIN connector receptacles 306, in accordance with an embodiment of the present specification. Referring to FIGS. 3A and 3B, the EMG equipment cart 300 comprises a mobile arm 302 holding the amplifier 305 comprising female DIN connector receptacles 306 for connecting with male DIN connector plugs (not shown in FIGS. 3A, 3B) coupled with electrodes (not shown in FIG. 3A, 3B) being used to monitor a patient's neural activity.

Figure 3C:
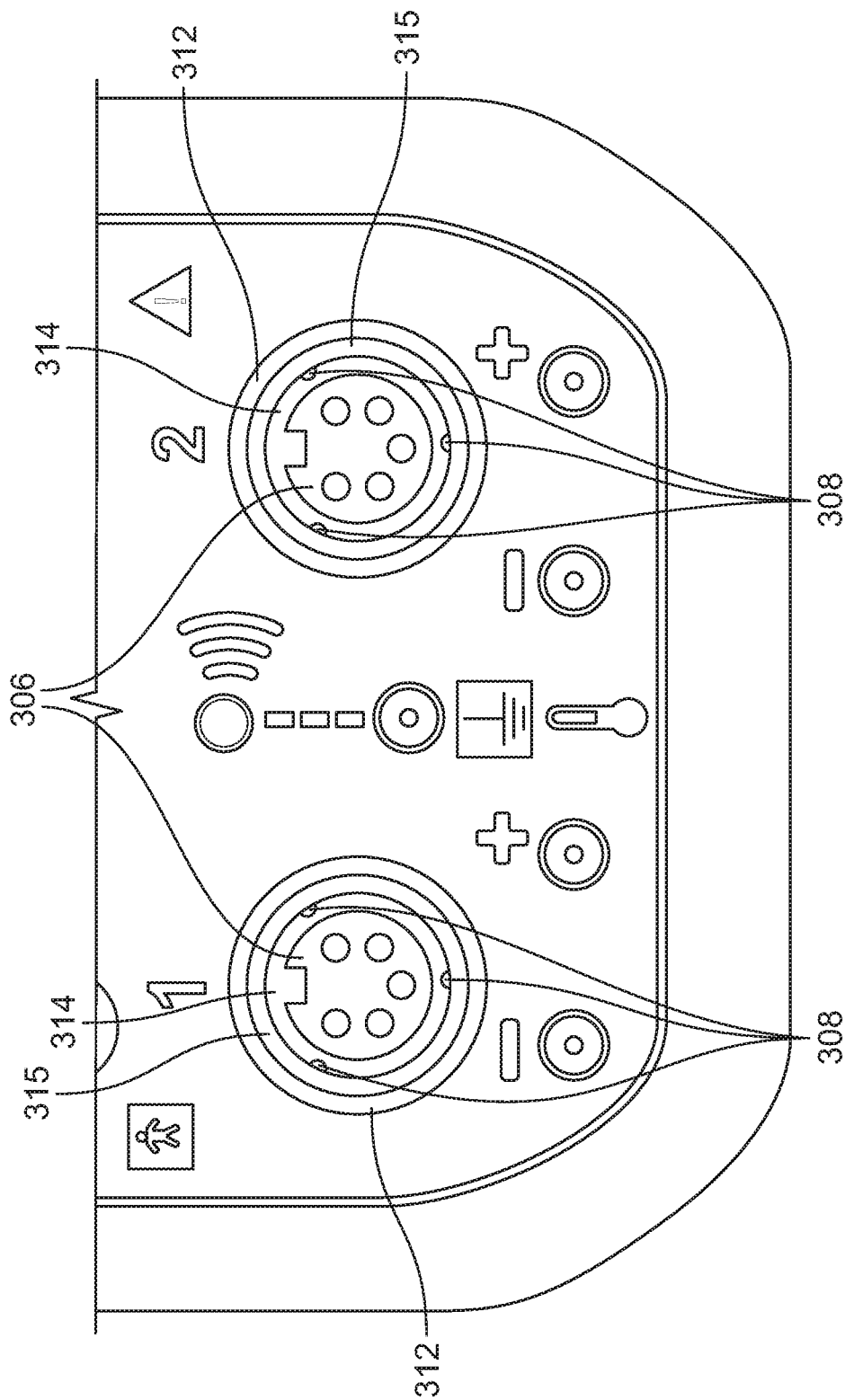
FIG. 3C illustrates a close up view of the female DIN receptacles of the amplifier shown in FIG. 3B.
Figure 3D:
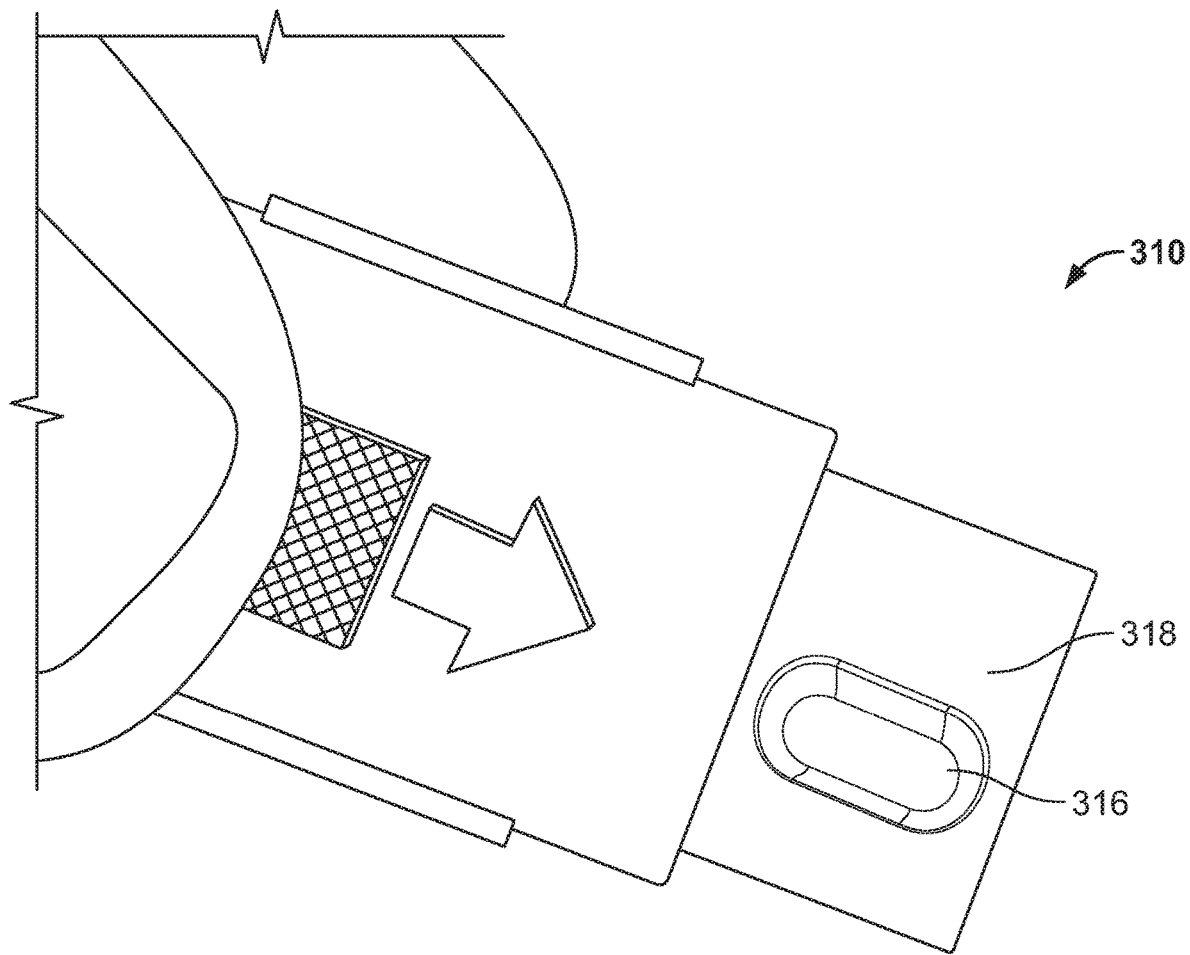
FIG. 3D illustrates a prior art male DIN plug that may be coupled with the male DIN receptacle of FIG. 3C, in accordance with an embodiment of the present specification.
Figure 3E:
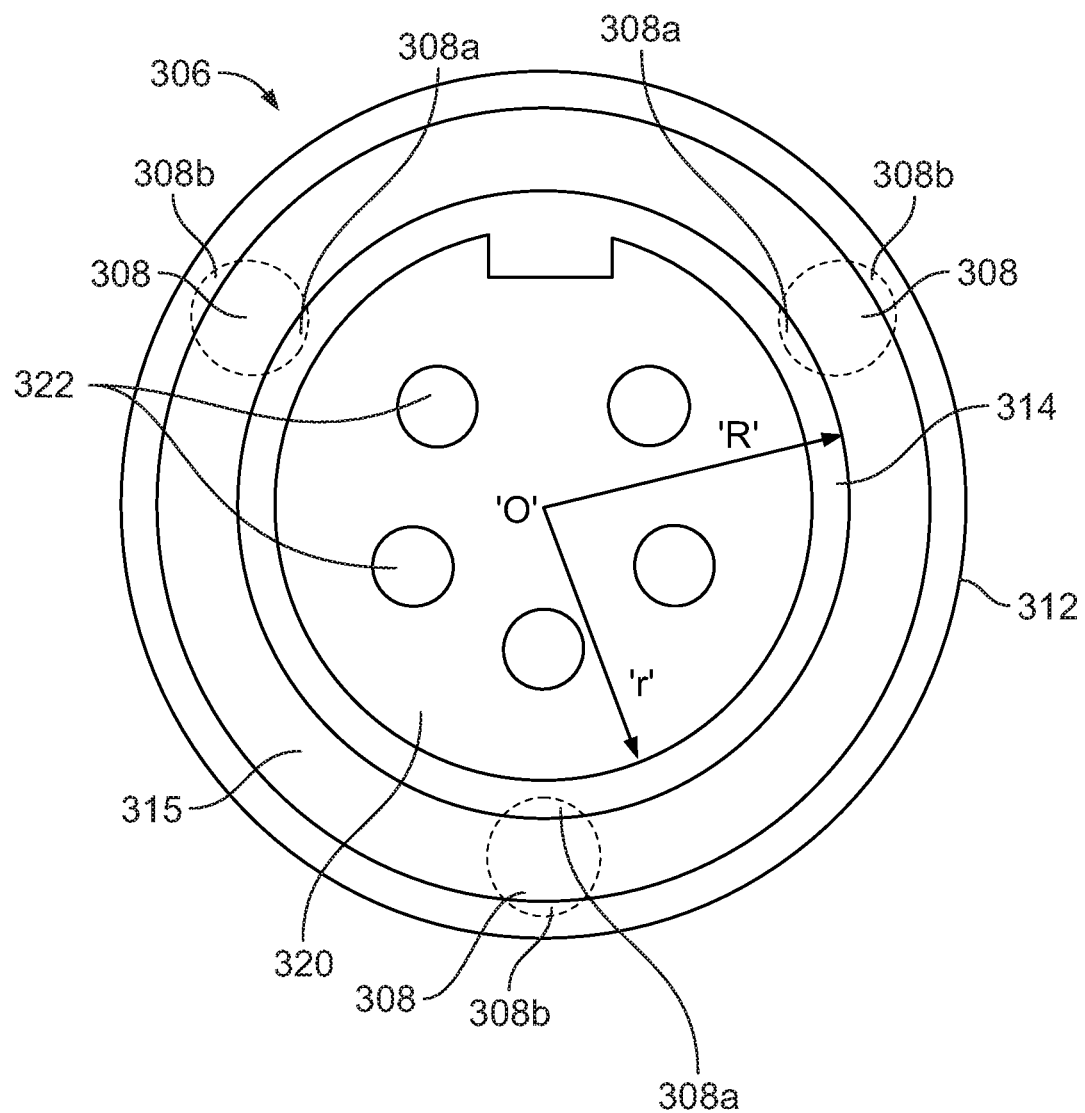
FIG. 3E is a top view cross sectional diagrammatical representation of a female DIN receptacle of FIG. 3C comprising 3 ball bearings, in accordance with an embodiment of the present specification.

FIG. 3C illustrates a close-up view of the female DIN receptacles 306 of the amplifier 304 shown in FIG. 3B. FIG. 3D illustrates a male DIN plug 310 that may be coupled with any one of the female DIN receptacles 306 of FIG. 3C, in accordance with an embodiment of the present specification. FIG. 3E is a top view cross sectional diagrammatical representation of the female DIN receptacle 306 of FIG. 3C comprising first, second and third protrusion members 308, in accordance with an embodiment of the present specification.

Referring to FIGS. 3C, 3D and 3E, each of the female DIN receptacles 306 comprises a circular housing 315 circumferentially surrounding a plug receptacle 320. The plug receptacle 320 comprises a plurality of hollow connector volumes 322 each of which is configured to receive a corresponding pin of the male DIN plug 310. In embodiments, an internal surface of the circular housing 315 is separated from the plug receptacle 320 by a circular gap, well or cavity 314. In some embodiments, the circular housing and the plug receptacle are molded.

In some embodiments, each of the female DIN receptacles 306 further comprises first, second and third protrusion members 308 positioned, respectively, in first, second and third gaps, spaces or notches within the circular housing 315. In some embodiments, the first, second and third protrusion members 308 are positioned 120 degrees from each other around the circular housing 315. In some embodiments, the first, second and third protrusion members 308 are ball bearings.

In some embodiments, the first, second and third ball bearings 308 press against a housing hood 318 of the corresponding male DIN plug 310 when the male DIN plug 310 and the female DIN receptacle 306 are mated.

In an embodiment, a spring force is achieved by using a circular retention band or an elastomeric O-ring 312, wherein the retention band 312 presses against each of the ball bearings 308. The circular retention band 312 is circumferentially positioned around an outside surface of the circular housing 315. The retention band 312 is configured to physically force the first, second and third protrusion members 308 out of their respective first, second and third gaps and further into the circular gap 314. In some embodiments, when the male DIN plug 310 is not inserted into the female DIN receptacle 306, the first, second and third protrusion members 308 are configured to be pressed against an outside surface of the plug receptacle 320 by the spring force provided by the retention band 312.

As shown in FIG. 3E, the circular gap 314 has an outer radius 'R' and an inner radius 'r' such that a width 'w' of the circular gap 314 is 'R-r'. In embodiments, each of the female DIN receptacles 306 has a first state and a second state. In the first state, the ball bearings 308 are positioned within the circular gap 314 such that X % of the width 'w' of the circular gap 314 comprises a ball bearing. In the second state, the ball bearings 308 are positioned within the circular gap 314 such that Y % of the width 'w' of the circular gap 314 comprises a ball bearing. In embodiments, Y % is less than X % when the first state corresponds to the male DIN plug 310 not being inserted into the female DIN receptacle 306 whereas the second state corresponds to the housing hood 318 of the male DIN plug 310 being inserted into the female DIN receptacle 306. Thus, in the first state the ball bearings are skewed radially towards a center 'O' of the female DIN receptacle 306 (as a result of being pushed by the retention band 312) causing the ball bearings 308 to occupy a higher percentage (X %) of the width 'w' of the circular gap 314. However, in the second state the ball bearings 308 are pushed radially away from the center 'O', by the inserted hood 318, against the retention band 312 causing the ball bearings 308 to occupy a lesser percentage (Y %) of the width 'w' of the circular gap 314.

Stated differently, in the first state the retention band 312 physically forces the first, second and third protrusion members 308 out of the respective first, second and third gaps and further into the circular gap 314 by a first distance. In the second state the retention band 312 physically forces the first, second and third protrusion members 308 out of the respective first, second and third gaps and further into the circular gap 314 by a second distance. The second distance is less than the first distance when the second state is achieved by the male DIN plug 310 being inserted into the female DIN receptacle 306.

In an embodiment, the ball bearings 308 are positioned approximately 1-3 mm from a top/opening surface of the female DIN receptacle 306. The proximity of the ball bearings 308 to the top/opening surface of the female DIN receptacle 306 allows the user to start the connector engagement process with no physical resistance. When the male DIN plug 310 is not seated in the female DIN receptacle 306, the ball bearings 308 are pushed-in toward the center '0' of the female DIN receptacle 306 (laterally), by the retention band 312, into the circular gap or space 314 configured to receive the housing hood or shell 318 of the male DIN plug 310.

Referring to FIGS. 3D and 3E, and similarly to the embodiment pictured in FIGS. 2A-2C, a first portion 308*a* (proximal to the center 'O' of the female DIN receptacle 306) of the ball bearings 308 extends into the gap 314 to contact the housing hood 318 of the male DIN plug 310 when inserted, while a second portion 308*b* (distal from the center 'O' of the female DIN receptacle 306) of the ball bearings 308, opposite the first portion 308*a*, contacts the compressible retention band 312. When the housing hood 318 of the male DIN plug 310 is inserted into the female DIN receptacle 306, the elastomeric retention band 312 applies pressure to the second portion 308*b* of the ball bearings 308, causing the ball bearings 308 to move laterally such that the first portion 308*a* of the ball bearings 308 contacts and applies a force to the housing hood 318, providing a more secure connection between the male DIN plug 310 and the female DIN receptacle 306.

In embodiments, the retention band 312 is stretched when positioned within the female DIN receptacle 306, so that it is in a tense state. In some embodiments, a dimensional relationship exists between a diameter of the ball bearing 308 and the size of the gap/opening 314 in the female DIN receptacle 306 and/or the housing hood or shell 318 of the male DIN plug 310 (outer circular portion of the male DIN plug 310 that inserts into the female DIN receptacle 306) to ensure that the male DIN plug 310 seats properly and securely within the female DIN receptacle 306. The diameter of the ball bearing 308 is designed such that it is not too large or small. Too large of a diameter will not allow the ball bearing 308 to be pushed aside as the male DIN plug 310 is inserted and too small of a diameter will not allow the ball bearing 308 to cause friction/resistance to hold the male DIN plug 310 in place. In an embodiment, the male DIN plug 310 comprises a dip/recess 316 to accommodate the ball bearing 308 so that the male DIN plug 310 'clicks' into place when seated in the female DIN receptacle 306 when the ball bearings 308 mate with the recess 316.

In various embodiments, the number of ball bearings and/or durometer rating of the retention band may be changed to modulate the force required to remove the male DIN plug from the male DIN receptacle.

The above examples are merely illustrative of the many applications of the system of present specification. Although only a few embodiments of the present specification have been described herein, it should be understood that the present specification might be embodied in many other specific forms without departing from the spirit or scope of the specification. Therefore, the present examples and embodiments are to be considered as illustrative and not restrictive, and the specification may be modified within the scope of the appended claims.

We claim:

1. A receptacle configured to receive a plug comprising a plurality of pins, wherein the receptacle comprises:
    a first housing having a circular enclosure wall defined by an exterior surface and an interior surface, wherein the interior surface of the enclosure wall encircles an interior space of the first housing, wherein the circular enclosure wall comprises at least one cavity;
    a plug receiver having an exterior surface and positioned within the interior space of the first housing, wherein the interior surface of the wall circumferentially surrounds the exterior surface of the plug receiver and is separated from the exterior surface of the plug receiver by a circular gap, and wherein the plug receiver comprises a plurality of connectors each configured to receive one of the plurality of pins of the plug;
    a first protrusion member positioned in the at least one cavity within the circular enclosure wall and configured to move when the plug is inserted into or removed from the plug receiver; and a retention band circumferentially positioned around the interior space and in physical communication with the circular enclosure wall, wherein the retention band is configured to physically force the first protrusion member out of the at least one cavity and into the circular gap.

2. The receptacle of claim 1, wherein the first protrusion member is a ball bearing.

3. The receptacle of claim 1, wherein the retention band is positioned within a groove extending circumferentially around the interior surface of the enclosure wall.

4. The receptacle of claim 1, wherein the receptacle is a female DIN connector receptacle.

5. The receptacle of claim 4, wherein the plug is a male DIN connector plug.

6. The receptacle of claim 1, wherein the first protrusion member is a ball bearing and wherein the ball bearing is made of stainless steel.

7. The receptacle of claim 1, wherein the receptacle is configured to connect EMG electrodes with an EMG control system via an amplifier.

8. The receptacle of claim 1, wherein the at least one cavity comprises a first cavity and a second cavity and further comprising a second protrusion member positioned in the second cavity, separate and distinct from the first cavity, within the circular enclosure wall.

9. The receptacle of claim 8, wherein the retention band is configured to physically force the second protrusion member out of the second cavity and further into the circular gap.

10. The receptacle of claim 8, wherein the first protrusion member and the second protrusion member are positioned 180 degrees from each other on opposite sides of the circular enclosure wall.

11. The receptacle of claim 8, wherein the first protrusion member is a ball bearing, the second protrusion member is a ball bearing, and both the first protrusion member and second protrusion member are configured to be pressed against an outside surface of the plug by a spring force provided by the retention band.

12. The receptacle of claim 1, wherein the first housing and the plug receptacle are molded.

13. The receptacle of claim 1, wherein the retention band is an O-ring having a durometer rating in a range of 50 to 90 Shore.

14. The receptacle of claim 1, further comprising a second protrusion member positioned in a second cavity, separate and distinct from the at least one cavity, within the circular enclosure wall and a third protrusion member positioned in a third cavity, separate and distinct from the second cavity and the at least one cavity, within the circular enclosure wall.

15. The receptacle of claim 14, wherein the retention band is an O-ring having a durometer rating in a range of 50 to 90 Shore.

16. The receptacle of claim 14, wherein the retention band is configured to physically force the second protrusion member out of the second cavity and further into the circular gap and to physically force the third protrusion member out of the third cavity and further into the circular gap.

17. The receptacle of claim 14, wherein the first protrusion member, the second protrusion member, and the third protrusion member are positioned 120 degrees from each other circumferentially around the circular enclosure wall.

18. A female receptacle configured to connect to a male plug, wherein the female receptacle comprises a first circular housing circumferentially surrounding a plug receptacle, wherein an internal surface of the first circular housing is separated from the plug receptacle by a circular gap and wherein the plug receptacle comprises a plurality of hollow connector spaces each configured to receive a pin of the male plug, the female receptacle further comprising:
    a first state wherein a first protrusion member is configured to be positioned in a first cavity within the first circular housing and a retention band is configured to be circumferentially positioned around a surface of the first circular housing and physically force the first protrusion member out of the first cavity and further into the circular gap by a first distance; and
    a second state wherein the first protrusion member is configured to be positioned in the first cavity within the first circular housing and the retention band is configured to be circumferentially positioned around the surface of the first circular housing and physically force the first protrusion member out of the first cavity and further into the circular gap by a second distance, wherein the second distance is less than the first distance and wherein the second state is achieved by inserting the male plug into the female receptacle.

19. The female receptacle of claim 18, wherein the first protrusion member is a ball bearing.

20. The female receptacle of claim 18, further comprising a second cavity, separate and distinct from the first cavity, in the first circular housing and a second protrusion member positioned in the second cavity within the circular enclosure wall.

21. The female receptacle of claim 20, wherein the retention band is configured to physically force the second protrusion member out of the second cavity and further into the circular gap.

* * * * *